| | | | |
|---|---|---|---|
| (12) | United States Patent <br> Wesselmann et al. | (10) Patent No.: <br> (45) Date of Patent: | US 8,430,844 B2 <br> Apr. 30, 2013 |

(54) BALLOON CATHETER

(75) Inventors: Matthias Wesselmann, Glattfelden (CH); Hans Lang, Buchs (CH); Susanne Pfenninger-Ganz, Aathal (CH); Adrian Blaser, Zurich (CH); Christoph Hannes Hoser, Zurich (CH); Horst Josef Fischer, Lauchingen (DE); Bodo Quint, Oberglatt (CH)

(73) Assignee: Biotronik AG, Buelach (CH)

( * ) Notice: Subject to any disclaimer, the term of this patent is extended or adjusted under 35 U.S.C. 154(b) by 85 days.

(21) Appl. No.: 13/023,921

(22) Filed: Feb. 9, 2011

(65) Prior Publication Data

US 2011/0202001 A1 Aug. 18, 2011

Related U.S. Application Data

(60) Provisional application No. 61/304,489, filed on Feb. 15, 2010.

(51) Int. Cl.
*A61M 29/00* (2006.01)

(52) U.S. Cl.
USPC .................................................... 604/101.02

(58) Field of Classification Search ............. 604/101.02, 604/103.08, 101.01, 102.01, 102.02, 102.03, 604/103, 103.06, 103.11, 103.14, 103.01; 606/192, 195
See application file for complete search history.

(56) References Cited

U.S. PATENT DOCUMENTS

| 5,108,525 | A | 4/1992 | Gharibadeh | |
|---|---|---|---|---|
| 5,342,305 | A * | 8/1994 | Shonk | 604/101.02 |
| 5,522,882 | A | 6/1996 | Gaterud et al. | |
| 7,217,278 | B2 | 5/2007 | Tomaschko et al. | |
| 8,043,259 | B2 * | 10/2011 | Radisch et al. | 604/103.08 |
| 2010/0030144 | A1 * | 2/2010 | Brunner et al. | 604/103.08 |

FOREIGN PATENT DOCUMENTS

| EP | 2149387 | 2/2010 |
|---|---|---|
| EP | 2 149 387 A1 | 3/2010 |
| GB | 2 046 096 A | 11/1980 |

OTHER PUBLICATIONS

European Search Report 11 15 1816.

* cited by examiner

*Primary Examiner* — Theodore Stigell
*Assistant Examiner* — Brooke Matney
(74) *Attorney, Agent, or Firm* — Biotech Beach Law Group PC

(57) ABSTRACT

A balloon catheter, including an outer shaft with a distal end and a fluid line, an inner part located distal anterior to its distal end, as well as a balloon that can be inflated under the influence of a fluid that has been pressurized by the fluid line, that is fastened fluid-tight onto the distal end section of the outer shaft with a first fastening zone at its proximal end, and fluid-tight onto inner part with a second fastening zone at its distal end, whereby the balloon, on at least one of its two ends is designed without cone and with essentially unvarying thin wall thickness, the balloon is provided on at least one of its two ends with respectively one twist anterior to its fastening zone, and a second balloon is placed above the first balloon and is also provided with a twist on at least one of its two ends anterior to the fastening zone, that is directed in the opposite direction of the twist of the first balloon end that is positioned underneath.

12 Claims, 1 Drawing Sheet

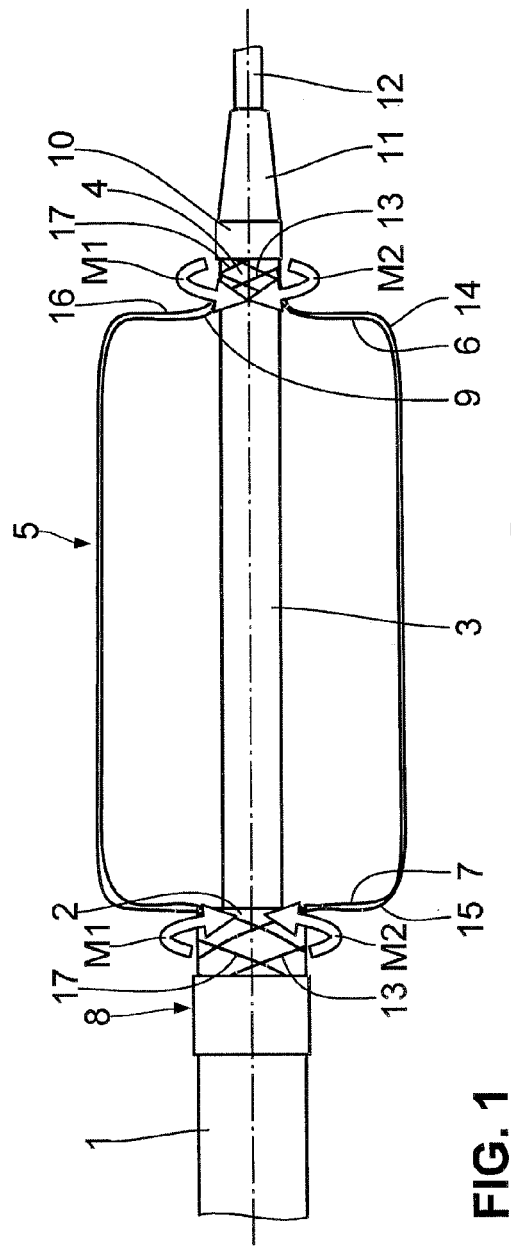
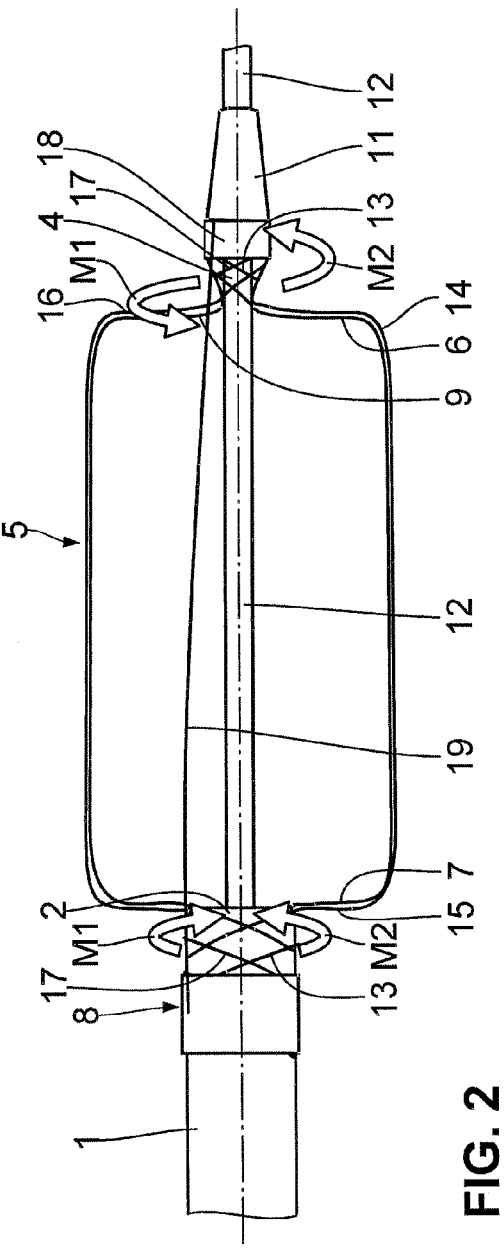
FIG. 1
FIG. 2

BALLOON CATHETER

CROSS REFERENCE TO RELATED APPLICATIONS

This invention claims benefit of priority to U.S. patent application Ser. No. 61/304,489, filed on Feb. 15, 2010; the contents of which are herein incorporated by reference in their entirety

TECHNICAL FIELD

The invention relates to a balloon catheter.

BACKGROUND OF THE INVENTION

A variety of balloon catheters are known, such as those provided in U.S. Pat. No. 5,522,882 A and U.S. Pat. No. 7,217,278 B2. Thus, balloon catheters, as they are used, perhaps for the enlargement of pathologically constricted vascular structures in the body or for the placement of vascular wall supports—so-called stents—have an outer shaft with a distal end and an inner shaft nested in it by forming a ring-shaped fluid line, that extends beyond the distal end of the outer shaft. At the distal end of the catheter, a balloon is fastened fluid-tight on the distal end section of the outer shaft at its proximal end in a first fastening zone, and with its second fastening zone at its distal end, fluid-tight to the distal end section of an inner part formed by the inner shaft. Between these fastening zones, the balloon is folded into longitudinal folds in non-inflated condition, so that its outer diameter is as small as possible in this condition. This is the prerequisite so that the balloon catheter with the balloon at the distal end can be slid forward, even through narrow vascular structures or very circumflex vascular areas. After placing the balloon at its site of insertion, a fluid can then be pressurized by the circular fluid line formed between the inner and outer shaft and the balloon can be inflated. Thereby, the longitudinal folds unfold in the direction of the periphery, thereby significantly enlarging the diameter of the balloon.

Because of the type of production and design, the balloons of conventional balloon catheters have disadvantages, which become clear in the following summary of the production process. Thus, as a rule, balloons are produced from an elastically stretchable plastic capillary tube with an outer diameter of, for example, 2.1 mm and a lumen diameter of, for example, 1.5 mm. The thickness of the wall of this capillary thus is 0.3 mm. Its ends are clamped into a retention device, whereupon the lumen is charged with a fluid pressure. Between the clamping points, the work piece is inflated and the wall material is drastically stretched, so that an essentially cylindrical balloon with a wall thickness of, for example, 0.03 mm is created. Starting at the clamped in ends of the balloon blank, the thickness of the wall over the cones at both ends of the balloon, decreases toward the casing wall, approximately by a factor of 10.

In a further processing step, the ends are still calibrated and, for example, brought to an outer diameter of 1.8 mm, as well as a lumen diameter of 1.6 mm. The thickness of the wall is then only just 0.1 mm and is thus still three times thicker than the thickness of the wall in the cylindrical part of the balloon blank.

If balloons produced in this way are now fastened with their ends on the outer shaft or inner shaft of the catheter and folded into longitudinal folds for the non-inflated condition, the ends and cones of the balloon contribute a significantly larger wall thickness than the very thin-walled cylinder casing of the balloon. The folded balloon profile is thus largest at the cones that form the balloon shoulders around the fastening zones. Correspondingly, the stiffness of the balloon is also most strongly developed there. Thus, these very thick end sections of the balloon impede an insertion of the catheter into narrow vascular structures. Beyond that, the stiffness of the balloon cones that are folded into folds makes guiding the balloon catheter around narrow curvatures or branches of vascular structures more difficult. Finally, in the production of the balloon catheter itself it is difficult to fold the cone sections that have thicker walls.

The previously mentioned U.S. Pat. No. 5,522,882 A reveals s stent positioning system with a catheter in which the inflatable balloon has ends that extend step-like. As a result of this, no cone sections of the balloon are to be present axially anterior to and posterior to the stent positioned on the catheter. This is achieved by means of sleeve-like top pieces that are directly adjacent to the stent on the balloon end sections, so that upon inflation of the balloon, the cones essentially turn into radial ring steps. The problem of the variable thickness of the wall and the folding of folds in conventional balloons is not addressed in this publication.

U.S. Pat. No. 7,217,278 B2 teaches an expensive subsequent processing of balloon blanks in that after inflation in the sections of the cones and the thick-walled ends, wall material is mechanically removed to decrease the thickness of the wall. Concerning this, particular attention must be paid to performing this processing step below the glass transition temperature of the thermoplastic plastic material. Overall, the production of such balloons as they are known from U.S. Pat. No. 7,217, 278 B2 is thus expensive from a technical perspective.

SUMMARY OF THE INVENTION

The invention is based on the problem of providing a balloon catheter in which by means of a simple design the thickenings and stiffenings that are present in prior art because of the cones that are folded into longitudinal folds can be avoided and simultaneously, a drastically increased bursting strength of the balloon arrangement can be achieved when it is inflated.

This problem is solved by the characteristics of Claim 1. For one, the principle of the solution provides that the balloon is formed without cones at least at one end, so that it is provided with unvaried, thin wall thickness extending over its entire length. In the fastening zones, the balloon is fastened fluid-tight onto the distal end section of the inner part, so that no thickening or stiffening of any kind appears at the distal end of the catheter.

Further, the ends of the inflatable balloon are thereby put into twists in the section anterior to the fastening zones of the balloon. Thus, the connection of the balloon toward the respective shaft is protected from so-called scalping load and the bursting sensitivity of the balloon is already fundamentally improved.

These approaches to a solution have already been described in the older, subsequently published application EP 2 149 387 of applicant.

For another, it is provided as an essential step of the present invention to place a second balloon without any cone over the first balloon, whereby this second balloon is likewise provided respectively with a twist at its two ends anterior to its fastening zone at the outer shaft or the inner part. The twists of the second outer balloon are thereby respectively directed in the opposite direction to those of the twists of the first balloon that is positioned underneath.

The operating mode of this step in accordance with the invention is to be explained as follows. As the result of the twisting of the balloon ends, in principle, a rotational moment is created upon the balloon sleeve during the inflation of the balloon, which tries to cancel the twisting. This mechanism is comparable to the unwinding of a candy wrapper at both twisted ends. As a result of the twists that are placed above each other directed in opposite direction of the two balloon covers, now, because of the opposite to the twistings also opposite opening moments at one end of the balloon are cancelled on the spot. The twistings also remain intact even during inflation of the balloon arrangement by inserting a pressurized fluid. Simultaneously, they act as a contraction, on account of which the two walls of the balloon that are opposite to each other support themselves more by the structure underneath the twisting. As a result, the fastening zones of the two balloons are protected from scaling load, the bursting strength of the balloon arrangement is thereby significantly increased further. Finally, this effect is further reinforced by the nesting arrangement of two balloon covers. Thus, a drastic overall increase of the bursting strength results within the meaning of the problem according to the invention.

Discernibly, such a balloon further has, over its entire length, comparably little thickening in diameter and no stiffening of any kind as the result of greater wall thickness in spite of twisting at its ends. Thus, such a balloon catheter can be guided without any problem through very narrow vascular structures and around narrow bends in a vascular system with its distal end that is provided with a balloon.

DESCRIPTION OF THE DRAWINGS

In the dependent claims, preferred embodiments of the balloon catheter are indicated, the characteristics of which, details and advantages are explained in more detail in the following description in conjunction with the enclosed drawings. Shown are:

FIG. 1 is schematic longitudinal cross sections of the distal end section of a balloon catheter in a first embodiment provided in inflated condition; and FIG. 2 is schematic longitudinal cross sections of the distal end section of a balloon catheter in a second embodiment provided in inflated condition.

DETAILED DESCRIPTION OF THE PREFERRED EMBODIMENTS

In conjunction with FIG. 1, the design of the balloon catheter in a first embodiment is described in more detail. Thereby, the basis is an essentially two-part catheter shaft formed by a tubular outer shaft 1 with a distal end 2, and with respect to its inner diameter significantly smaller inner shaft 3, whose distal end 4 extends at least by the length of the balloon arrangement 5 beyond the distal end 2 of the outer shaft 1. Between the outer and the inner shaft 1, 3, a ring-shaped fluid line (not shown) is formed by means of which a corresponding pressurized fluid can be conveyed into the balloon arrangement 5.

The balloon arrangement 5 consists of an inner balloon 6 that is mounted pressure-tight with its proximal end 7 in a fastening zone 8 anterior to the distal end 2 of outer shaft 1, for example, by welding or adhesion. Analogous to that, its distal end 9 is mounted pressure-tight on the distal end 4 of inner shaft 2 in a corresponding fastening zone 10 by welding or adhesion. The fastening zone 10 is thereby located proximally anterior to the conically designed end piece 11 of the inner shaft 3. If further has a (not shown) lumen for a guide wire 12.

As indicated in FIG. 1, the two ends 7, 9 of the inner balloon 6 are respectively placed anterior to the fastening zones 8, 10 in twist 13 that is indicated by sloped lines.

A second outer balloon 14 is located above inner balloon 6, which is in turn fixated pressure-tight with its proximal end 15 in the fastening zone 8 correspondingly by welding or adhesion. Even the distal end 16 of this outer balloon 14 is fixated in the second fastening zone 10 at the inner shaft 3.

As is indicated by the sloped lines that run in opposite direction to the twist 13, the outer balloon 14 is in turn configured twisted anterior to the two fastening zones 8, 10 by twist 17 that is directed in the opposite direction to twist 13.

In the folded condition that is not shown in FIG. 1, the balloons 6, 14 are placed tightly onto the inner shaft in longitudinal folds, so that the balloon arrangement 5 remains narrow in diameter and does not significantly extend radially beyond the diameter dimension of the outer shaft 1.

If the balloon arrangement 5 is transitioned as per FIG. 1 by inserting a pressurized fluid by means of the—not shown—ring line between inner and outer shaft 3, 1 into the inflated condition shown in FIG. 1, as the result of the twists in opposite direction 13, 17 of the two balloons 6, 14, opposite rotational moments M1, M2 are created respectively that cancel each other. Simultaneously, the balloons 6, 14 in the section of the twists 13, 17 are thereby pulled together and they position themselves force-fit onto the outer or inner shaft 1, 3. As a result, the two fastening zones 8, 10 are relieved from the scaling forces created by the inflation of the balloon arrangement 5. Thus, overall, an extremely burst-resistant balloon arrangement results.

It is to be noted that the twisted connection in FIG. 1 can also be implemented only at one end of the balloon, either distal or proximal so that, for example, the second balloon end looks like a conventional balloon cone.

The "strangulation effect" described above during the inflation of the balloon arrangement 5 by means of pulling together balloons 6, 14 in the section of their twists 13, 17, also opens up the possibility of implementing completely new balloon catheter designs. A possible catheter design that is completely different from previous catheters with inner and outer shaft is shown in FIG. 2. This balloon catheter only has one outer shaft 1 that is provided only with one lumen for the guide wire 12 and one line for the pressurized fluid for inflating the balloon arrangement 5. Instead of an inner shaft, the balloon catheter in accordance with FIG. 2 is provided only with the end piece 11 as a type of inner part, onto which the two balloons 6, 14 are fixated with their distal ends 9, 16 in a fastening zone 18 by welding or adhesion. Anterior to this fastening zone 18, the two balloons 6, 14 are placed again into twists 13, 17 in opposite direction, whereby in this section, there are no longer any structural sections of the end piece 11 inside the balloons.

Analogous to the example of an embodiment as per FIG. 1, the proximal ends 7, 15 are fixated pressure-tight in the fastening zone 8 at outer shaft 1 by welding or adhesion, and are also provided there with twists the 13, 17 in opposite directions.

Finally, in FIG. 2, a connection cross tie designed as individual wire of nitinol is provided between the distal end 2 of the outer shaft 1 and the end piece 11. It can also be provided as a multiple wire arrangement or a type of wire corset. This connection cross tie 19 extends outside of the balloon arrangement 5 essentially parallel to the longitudinal axis of the balloon catheter.

In the balloon catheter without inner shaft as per FIG. 2, the sealing of the interior of the balloon is performed during the inflation, as the balloon arrangement 5 in the area of the distal twists 13, 17 seals by means of the direct constriction or strangulation effect on guide wire 12 that was described, whereby in turn as a result of the twists 13, 17, the reciprocal cancellation of moments M1, M2 takes place anterior to the two fastening zones 8, 18.

Overall, the balloon catheter shown in FIG. 2 can reliably be slid along the guide wire 12, thus it has sufficient "pushability". Further as a result of the connection tie/s, during the inflation of the balloon arrangement 5, a so-called "scoring function" can be achieved, i.e. stenoses can, as it were, be broken open by means of the wire-shaped connection ties.

Because there is no inner shaft in the balloon and the guide wire extends freely through the balloon, the balloon catheter of the solution illustrated in FIG. 2 can be produced with a significantly smaller profile.

Finally, the balloon catheter shown in FIG. 2 can be used for releasing substances such as contrast agents in the case of diagnostic catheters, which can be discharged into its lumen after retracting the guide wire 12 by means of the catheter and the opening in end piece 11.

Deviating from the two variants introduced (FIG. 1 and FIG. 2), the outer shaft can also be welded edgeless onto the twisted proximal end of the balloon (no illustration). Then the twisted balloon end will pull itself together subject to the interior pressure and severely limit the deflatability or eliminate such entirely. To prevent this, at least one capillary must be provided in the design between the twisted end and the inner part, which decreases the interior pressure in the balloon again by means of a leakage flow until the twisted balloon end can open itself again. This capillary can, for example, be created by a chamfer in the inner shaft.

A further case of application for the two above balloon catheters with self-sealing balloons under pressure is, for example, the construction of inflatable implants, which take on the support and sealing functions.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A balloon catheter, comprising:
   a) an outer shaft with a distal end and a fluid line;
   b) an inner part located distal anterior to its distal end; and
   c) a balloon that can be inflated under the influence of a fluid that has been pressurized by the fluid line, that is fastened fluid-tight onto a first end section of outer shaft with a first fastening zone at its proximal end, and fluid-tight onto the inner part at its distal end with a second fastening zone;
   characterized by, that
      the balloon, on at least one of its two ends is designed without cone and with essentially unvarying thin wall thickness,
      the balloon is provided at least on one of its two ends with respectively one twist anterior to its fastening zone, and
      a second balloon is placed over the first balloon and is also provided with a twist on at least one of its two ends anterior to the fastening zone, that is directed in the opposite direction of the twist of the first balloon that is positioned underneath.

2. The balloon catheter according to claim 1, wherein the two balloons are welded or glued in the fastening zones at both ends.

3. The balloon catheter according to claim 1, wherein the twists of the two balloons extend into fastening zones.

4. The balloon catheter according to claim 1, wherein the inner part is designed as distal inner shaft that extends beyond the outer shaft.

5. The balloon catheter according to claim 1, wherein the inner shaft is provided with a guide wire lumen.

6. The balloon catheter according to claim 1, wherein the inner part comprises a tip component, distal anterior to the distal end of outer shaft.

7. The balloon catheter according to claim 6, wherein the tip component is provided with a guide wire lumen.

8. The balloon catheter according to claim 7, wherein the distal twists of the two balloons are located proximal anterior to the tip component.

9. The balloon catheter according to claim 8, wherein the balloons with their distal twists are configured in such a way, that when they are pressurized for inflating the balloons, they seal pressure-tight with the guide wire that is located in the guide wire lumen of the tip component.

10. The balloon catheter according to claim 6, wherein the tip component is connected by at least one connection tie with the distal end of outer shaft.

11. The balloon catheter according to claim 10, wherein the connection tie extends outside of the balloons.

12. The balloon catheter according to claim 11, wherein the connection tie is designed as wire.

* * * * *